United States Patent

Cox et al.

[11] Patent Number: 5,097,728
[45] Date of Patent: Mar. 24, 1992

[54] BIOPSY FORCEPS JAW AND METHOD FOR MAKING IT

[76] Inventors: Dennis Cox, 25479 Sheffield La., Saugus, Calif. 91350; Lanita Cox, 25059 Wintergreen Ct., Newhall, Calif. 91381

[21] Appl. No.: 586,852

[22] Filed: Sep. 21, 1990

[51] Int. Cl.⁵ .............................................. B21K 5/12
[52] U.S. Cl. ....................................................... 76/119
[58] Field of Search ................ 128/751; 606/205, 206, 606/207; 76/101.1, 119, 104.1

[56] References Cited

U.S. PATENT DOCUMENTS 2,028,558  1/1936  Nietzel et al. ........................ 76/104.1

Primary Examiner—Roscoe V. Parker
Attorney, Agent, or Firm—Donald D. Mon

[57] ABSTRACT

A method of forming a jaw for biopsy forceps with a very sharp edge. An initially flat metal plate is first relieved to form a recessed area extending along an edge. The edge is then honed sharp. Finally the plate is folded to bring the relieved areas into facing relationship to form a cup whose sharp edge extends along the edge of the cup, including around the bight formed by the bend.

1 Claim, 1 Drawing Sheet

BIOPSY FORCEPS JAW AND METHOD FOR MAKING IT

FIELD OF THE INVENTION

This invention relates to jaws for biopsy forceps, and to a method for making them.

BACKGROUND OF THE INVENTION

Jaws for biopsy forceps have a cup with a sharp edge. The sharp edge cooperates with an edge of another jaw to sever tissue which is received in the cup. This is a common construction for biopsy forceps. The problem is that the manufacture of these jaws is costly and the resulting product, especially its sharp edge, is less than optimum. This is because of the difficulty of making a sharp edge on a very small cup.

It is an object of this invention to provide a biopsy forceps jaw which can be made with a very sharp edge, and at a markedly lesser cost than known jaws of this type.

BRIEF DESCRIPTION OF THE INVENTION

To form a cup with a sharp edge according to this invention, an initially flat metal plate is relieved to form a recessed area extending along an edge. The edge is then honed sharp. The relief can be formed by stamping, or preferably by etching.

Then the plate is folded to bring relieved areas into facing relationship to form a cup whose sharp edge extends along the edge of the cup, including around the bight formed by the bend. This edge is as sharp as it was honed, and the honing was accomplished on a straight edge, rather than on a curved edge.

The resulting shape can be modified to suit a later incorporation into an instrument, either after the cup is formed, or before it is formed.

There is thus provided an optimally sharp-edged cup, economically formed by simple honing and folding operations.

Detailed Description fo the Drawings

Figure 1:
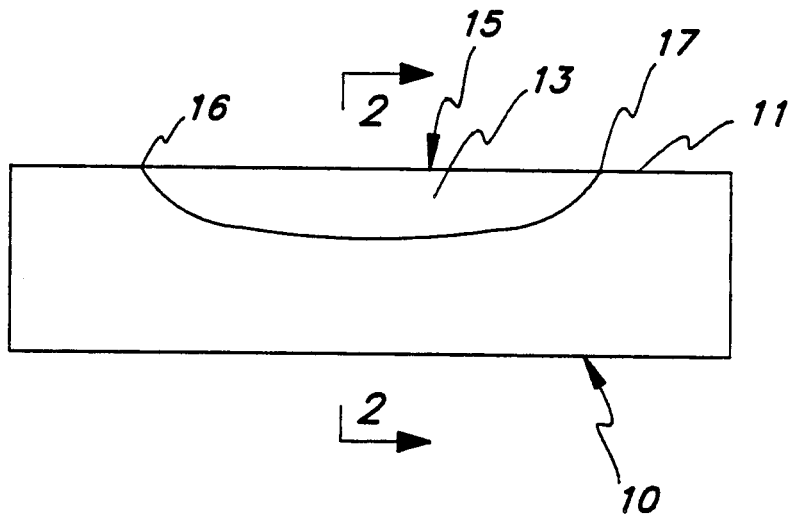
FIG. 1 is a plan view of a blank prepared for folding into a cupped configuration.

FIG. 1 shows a blank 10 comprising of a flat sheet of metal having a straight edge 11, a flat surface 12, and a recess 13 extending partway along edge 11. The recess can be formed by a stamping operation, but more often and preferably it will be formed by etching. It is deepest along edge 11 and becomes shallower as it blends into surface 12.

Figure 2:
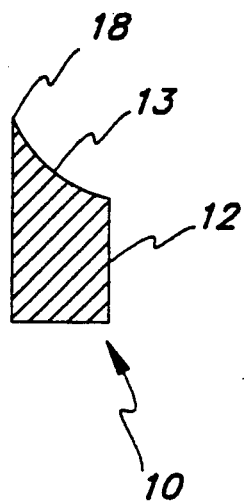
FIG. 2 is a cross-section taken at line 2—2 in FIG. 1

Portion 15, between edge ends 16, 17 of the recess, is honed to form a sharp cutting edge 18 best shown in FIG. 2.

Figure 3:
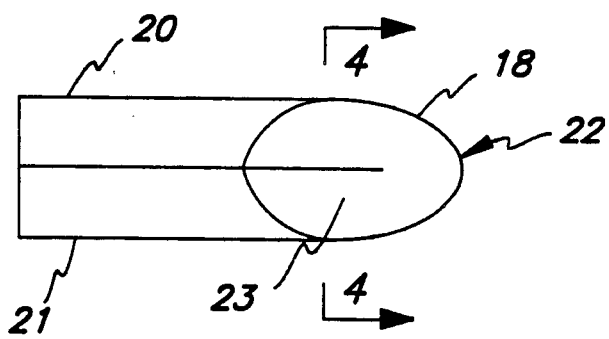
FIG. 3 is a top view of the blank of FIG. 1 folded to form a cup.
Figure 4:
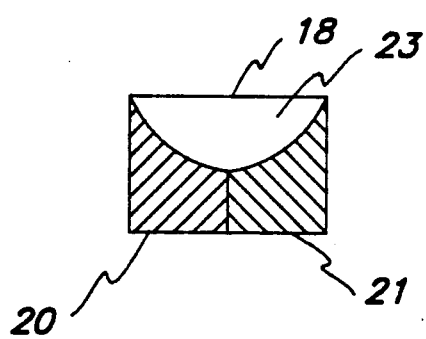
FIG. 4 is a cross-section taken at 4—4 in FIG. 3.
Figure 5:
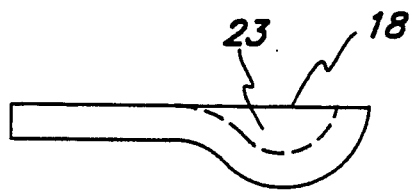
FIG. 5 is a side view of a finally prepared jaw.

To form the jaw, the plate is folded around section line 2—2 to form the structure shown in FIGS. 3 and 4. Accordingly, the structure now has two arms 20, 21 which lie flat against each other, and a bight 22 joining them. The arms are in facing relationships. Then cutting edge 18 extends around cup 23 which was formed when the blank was folded. There results a cupped structure which can be modified by trimming away excess material, as shown in FIG. 5.

Alternatively, the blank could be cut to shape before folding the plate. The arms can be joined together in any desired way, for example adhesively, with fasteners, or by welding.

The resulting structure is a cup with an elegant and very sharp jaw formed by inexpensive procedures. The resulting product is much less expensive, and is as good as or better than the cutting edges of conventional jaws, because the honing action was formed on a linear body rater than on a previously-formed body. The folding action does not adversely affect the sharpness.

This invention is not to be limited by the embodiment shown in the drawings and described in the descriptions which is given by way of example and not of limitation, but only in accordance with the scope of the appended claims.

We claim:

1. The method for forming a jaw for a biopsy forceps comprising:

in a flat metal blank having a straight boundary edge and a flat surface on each side of said strait edge, forming a recess along a portion of said edge deepest contiguous to said edge, and becoming shallower as it extends away from said edge;

honing said portion to form a sharp cutting edge along said boundary edge;

bending said blank to form a fold at a fold location along said cutting edge to bring into contiguity those portions of the said surface on opposite sides of said fold;

whereby to form a cup with a sharp peripheral cutting edge externally along a bight formed by the bent cutting edge.

* * * * *